United States Patent [19]
Omura et al.

[11] Patent Number: 5,756,320
[45] Date of Patent: May 26, 1998

[54] BIOACTIVE SUBSTANCES K93-0711 I-1 AND I-2 AND PROCESS FOR PRODUCTION THEREOF

[75] Inventors: Satoshi Omura; Kanki Komiyama; Masahiko Hayashi; Satoshi Takamatsu, all of Tokyo, Japan

[73] Assignee: The Kitasato Institute, Tokyo, Japan

[21] Appl. No.: 785,767

[22] Filed: Jan. 21, 1997

[30] Foreign Application Priority Data

Jan. 19, 1996 [JP] Japan ................... 8-007521

[51] Int. Cl.[6] ............... C12P 17/00; C12P 17/16; C12P 1/20; C07D 209/56
[52] U.S. Cl. ................ 435/117; 435/118; 435/253.5; 435/261; 435/886; 548/427; 548/428; 548/430; 548/432
[58] Field of Search .................. 548/428, 429, 548/430, 432; 435/253.5, 261, 886, 71.1, 117, 118

[56] References Cited

FOREIGN PATENT DOCUMENTS 3-41069  2/1991  Japan .

OTHER PUBLICATIONS

A. Kawashima, et al., "Preparation of Fluorinated Antibiotics Followed by $^{10}$F NMR Spectroscopy", The Journal of Antibiotics, vol. XXXIX No. 10, Oct. 1986, pp. 1495–1497.

I. Saito, et al., "Peroxidic Intermediates in Indole–Singlet Oxygen Reactions; Mechanism of the $C_2$–$C_3$ Ring Cleavage of Tryptophol", Feb. 1978, pp. 531–534.

Y. Nihel, et al., "Epocarbazolins A and B, Novel 5–Lipoxygenase Inhibitors", The Journal of Antibiotics, vol. 46, No. 1, 1992, pp. 25–33.

J. R. Anderson et al., "Punctatins B & C(Antibiotics M95154 and M95155): Further Sesquiterpene Alcohols from the Fungus Poronia punctata", J. Chem. So., Chem., Commun., 1984, pp. 917–919.

T. Yamashita et al., "Isolation of a new Indole Alkaloid, Pendolmycin, from Nocardiopsis", Journal of Natural Products, vol., 51, No. 6, Nov–Dec. 1988, pp. 1184–1187.

J. H. Rigby et al., "Convergent Total Synthesis of (±) Tenellin", J. Org. Chem., vol. 54, 1989, pp. 5852–5853.

M. Norte et al., "Three New Bromo Ethers from the Red Alga Laurencia Obtusa", Tetrahedron, vol. 45, No. 18, 1989, pp. 5987–5994.

R. E. Schwartz et al., "Pramanicin, a Novel Antimicrobial Agent from a Fungal Fermentation", Tetrahedron, vol. 50, No. 6, 1994, pp. 1675–1686.

V. R. Hegde et al., "Isolation and Structure of two novel Muscarinic Receptor Antagonists", Journal of Natural Products, vol. 58, No. 6, Jun. 1995, pp. 843–847.

M. Benn et al., "Hetisine 13–0–Acetate, A New Diterpenoid Alkaloid from *Delphinium Nuttallianum* Pritz", Heterocycles, vol. 24, No. 6, 1986, pp. 1605–1607.

D. W. Hughes et al., "C magnetic resonance spectra of some isoquinoline alkaloids and related model compounds", Can. J. Chem., vol. 54, 1976, pp. 2252–2260.

Sun Fang et al., "A new $C_{20}$–Diterpene Alkaloid, Spirasing III and the Interconversion of Oxazolidine Ring", Heterocycles, vol. 26, No. 1, 1987, pp. 19–23.

V. D. Gorbunov, "Structure of spireine", Chemical Abstracts, vol. 72, 1970, p. 67159.

Yang–Chang Wu et al., "Thalicsessine, A. new $C_{20}$–Diterpenoid Alkaloid from Thalictrum Sessile Hayata", Heterocycles, vol. 26, No. 4, 1987, pp. 943–943.

M. Leboeuf et A. Cave, "Alcaloides Des Ecorces De L'Uvariopsis Guineensis", Phytochemistry, 1972, vol. II, pp. 2833–2840.

Masahiko Hayashi et al., The Journal of Antibiotics., vol. 49, No. 11, pp. 1091–1095, 1996.

*Primary Examiner*—Ponnathapura Achutamurthy
*Assistant Examiner*—Padmashri Ponnaluri
*Attorney, Agent, or Firm*—Young & Thompson

[57] ABSTRACT

Bioactive substances K93-0711 I-1 and I-2 having inhibitory action on IL-6 activity, are produced by culturing a microorganism belonging to the genus Streptomyces in a medium, whereby the bioactive substances K93-0711 I-1 and I-2 accumulate in the medium. These bioactive substances K93-0711 I-1 and I-2 are then isolated therefrom. The substances are effective for treatment of IL-6-involving diseases such as cancer cachexia, multiple myeloma and rheumatoid arthritis.

9 Claims, 8 Drawing Sheets

BIOACTIVE SUBSTANCES K93-0711 I-1 AND I-2 AND PROCESS FOR PRODUCTION THEREOF Field of the Invention The present invention relates to bioactive substances K93-0711 I-1 and I-2 and a process for production of the bioactive substances K93-0711 I-1 and I-2 by culturing a microorganism having an ability to produce the same, wherein the substances have a suppressive action for the growth of IL-6-dependent MH-60 (hereinafter designated as MH-60) cells.

Background of the Invention

Treatments for cancer mainly comprise surgical operations, radiation therapy and chemotherapy. Progress in these therapies and the development of new anticancer agents have resulted in a cure rate for cancer of up to 50%. Gastric cancer and uterine cancer are often found by mass examination or periodic medical check-ups and the mortalities thereof have correspondingly decreased. However, recent changes of food and living conditions and the aging of society have resulted in an increase of lung cancer, liver cancer, cancer of the colon and prostate cancer. These cancers have a tendency to be accompanied by malignancy and to cause metabolic changes collectively known as cachexia. No effective chemotherapic agents for cancer cachexia have been found.

Progressing toward a cure rate above 50% for cancer, importance must be given to the quality of life (QOL). For Example, cancer cachexia is attended by constant functional disorders (metabolic, endocrine and immunologic abnormalities) often observed in cancer patients, and various symptoms such as body weight loss, adipose and muscular tissue weight loss and hypercalcemia. Cachexia causes a decrease in the QOL of the patients as well as a shortening of the life span, an increase in the rate of recurrence and a decrease in the response to anticancer agents, and results in a poor prognosis. Chemotherapeutic agents with improved action for cachexia have been sought in order to cure and to prevent postoperative recurrence and a poor prognosis.

The causes of cacnexia are unknown. However, recent studies indicate that excess production of interleukin-6 (hereinafter designated as IL-6), a type of cytokine, is involved in cachexia. Therefore, a substance having inhibitory action on IL-6 activity and suppressive action of the production of IL-6, is assumed to have improved activity against cachexia.

Summary of the Invention

The present invention provides novel bioactive substances K93-0711 I-1 and I-2 [the compound has been given a generic name madindoline, refer to *J. Antibiotics*, 49(11): 1091–1095, 1996] which is an inhibitor of IL-6 activity.

The present invention also provides a process for the production of the novel bioactive substances K93-0711 I-1 and I-2 comprising culturing a microorganism having an activity of producing bioactive substances K93-0711 I-1 and I-2 belonging to the genus Streptomyces, in a medium, accumulating the bioactive substances K93-0711 I-1 and I-2 in the cultured medium, and isolating the bioactive substances K93-0711 I-1 and I-2 therefrom.

Detailed Description of the Invention

Figure 1:
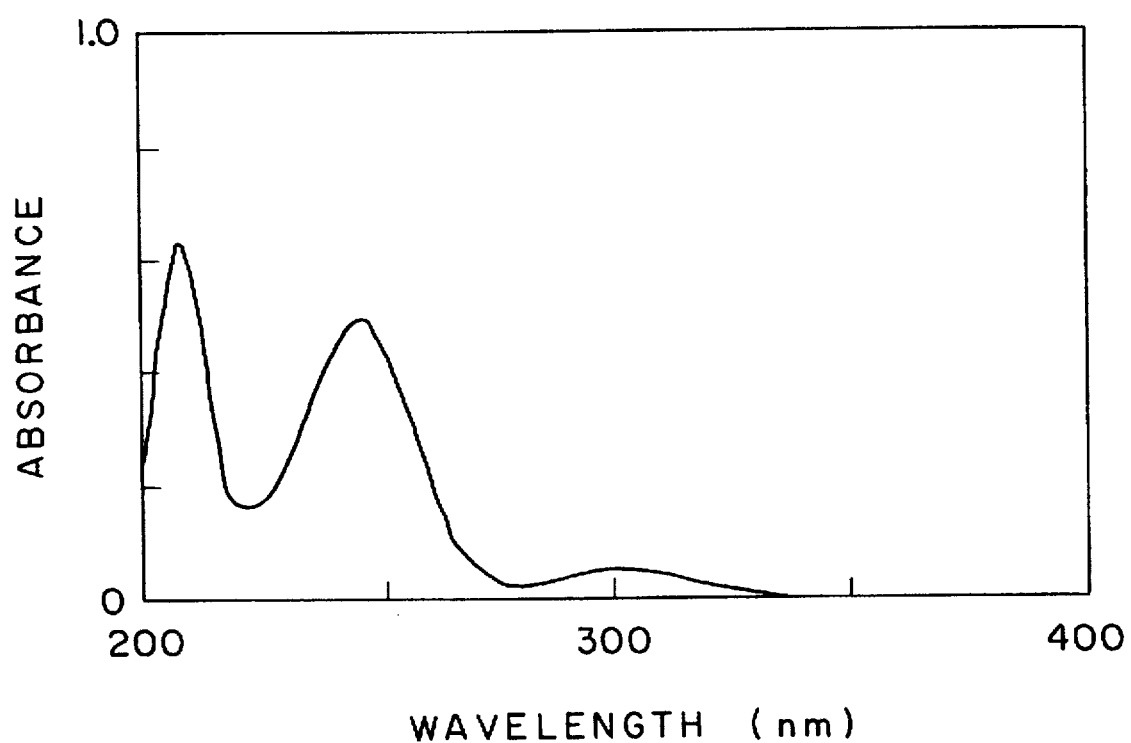
FIG. 1 is the UV absorption spectrum of the bioactive substance K93-0711 I-1 (in methanol)

We have found that selective growth inhibition against MH-60 cells was detected in fermentation extracts of microbial strain K93-0711 from soil. The effective substances were isolated from the cultured medium and purified. The said substances have not been reported in the literature and were designated K93-0711 I-1 and I-2.

The strain of microorganism for the production of bioactive substances K93-0711 I-1 and I-2 of the present invention is Streptomyces sp. K93-0711 I-1 which was isolated by the present inventors. The taxonomical properties of the strain are as follows:

I. Morphological properties:

The vegetative mycelia grew abundantly on various agar media and showed bacillary elements. The aerial mycelia grew abundantly on oatmeal agar and glycerol-asparagine agar. The aerial mass color was white to gray. The spore chains were Retiflexibiles type and each had more than 20 spores per chain. The spores were cylindrical in shape, 1.4×0.7 µm in size, and had a smooth surface. Sclerotic granules, sporangia and flagellated spores were not observed.

II. Cultural characteristics on various media:

The cultural characteristics of the present strain were investigated by the method of E. B. Shirling and D. Gottleib (*Int. J. Syst. Bacteriol.*16: 313–340, 1966) and the results are shown in Table 1.

The Color Harmony Manual, 4th Ed., 1958 (Container Corp. of America, Chicago) was used for color names and hue numbers. Cultures were observed after incubation at 27° C. for 2 weeks.

TABLE 1

| Cultural characteristics of strain K93-0711 | | | | |
|---|---|---|---|---|
| Medium | Growth | Reverse color | Aerial mass color | Soluble pigment |
| Sucrose-nitrate agar** | Moderate, ivory tint (2cb) | Ivory tint (2cb) | Poor, pearl (2ba) | None |
| Glucose-asparagine agar | Moderate, pearl pink (3ca) | Pearl pink (3ca) | Poor, pearl (2ba) | None |
| Glycerol-asparagine agar* | Good, natural (2dc) | Natural (2dc) | Abundant, silver, gray (3fe) | None |
| Inorganic salts-starch agar* | Moderate, bamboo (2gc) | Lt. mustard tan (2ie) | Moderate, covert gray (2fe) | None |
| Tyrosine agar* | Moderate, lt. brown (3lg) | Lt. brown (3lg) | Moderate, natural (2dc) | Lt. brown (3lg) |
| Oatmeal agar* | Good, bamboo (2gc) | Bamboo (2gc) | Moderate, gray (2fe) | None |
| Yeast | Good, | Biscuit | Abundant, | None |

TABLE 1-continued

Cultural characteristics of strain K93-0711

| Medium | Growth | Reverse color | Aerial mass color | Soluble pigment |
|---|---|---|---|---|
| extract-malt extract agar* | lt. mustard tan (2ie) | (2ec) | covert gray (2fe) | |
| Nutrient agar** | Moderate, putty (1½ec) | Ivory (2db) | Moderate alabaster tint-pearl gray (13ba–13dc) | None |
| Peptone-yeast extract-iron agar** | Moderate, lt. mustard tan (2ie) | Lt. mustard tan (2ie) | None | Lt. brown (3lg) |
| Glucose-nitrate agar** | Moderate, biscuit (2ec) | Bamboo (2gc) | Moderate alabaster tint (13ba) | None |
| Glycerol-calcium malate agar** | Good, covert tan (2ge) | Bamboo (2gc) | Abundant, alabaster tint–gray (13ba–i) | None |
| Glucose-peptone agar** | Good, mustard tan (1 ½ lc) | Golden brown (3pg) | Abundant, alabaster tint (13ba) | None |

*Medium recommended by International Streptomyces Project
**Medium recommended by S. A. Waksman.

III. Physiological properties:
  (1) Melanin formation
    (a) Tyrosine agar −
    (b) Peptone-yeast −
    (c) Tryptone-yeast −
  (2) Tyrosinase reaction −
  (3) $H_2S$ production −
  (4) Nitrate reduction +
  (5) Liquefaction of gelatin (21°–23° C.) +
    (glucose-peptone-gelatin agar)
  (6) Hydrolysis of starch +
  (7) Coagulation milk (37° C.) −
  (8) Peptonization of milk (37° C.) +
  (9) Temperature range for growth 15°–39° C.
  (10) Utilization of carbon sources
    (Pridham and Gottlieb's agar medium)
    utilized: glucose, arabinose, xylose and rhamnose
  (11) Cellulolytic activity
IV. Chemical composition:
  The DAP isomer in whole-cell of the strain in LL-type.

The taxonomic properties of the present strain K93-0711 are summarized as follows:

The DAP isomer in whole-cells in LL-type. The vegetative mycelia grew abundantly on various agar media, and show bacillary elements. The aerial mycelia are straight, forming long spore chains. The surface of the spores is smooth. The vegetative mycelia show a brown color on various media and the mass color of the aerial mycelia is white to gray. The soluble pigment formation is slightly brownish in Tyrosine agar and peptone-yeast extract iron agar.

Based on the taxonomic properties described above, strain K93-0711 is considered to belong to the genus Streptomyces. The strain is referred to as Streptomyces sp. K93-0711, and was deposited in the National Institute of Bioscience and Human Technology Agency of Industrial Science and Technology, Japan, as Streptomyces sp. K93-0711, whose accession No. is FERM P-15253. The strain was transferred to the international deposit of microorganisms based on the Budapest Treaty on the International Recognition of the Deposit of Microorganisms for the Purposes of Patent Procedure on Dec. 4, 1996 as accession No. FERM BP-5764. The depositor is The Kitasato Institute of 9-1, Shirokane 5-chome Minato-ku, Tokyo.

The strain of the present invention for the production of the bioactive substances K93-0711 I-1 and I-2 was described hereinabove. However, the general properties of Streptomyces are known to mutate easily by using, for example ultraviolet, X-ray irradiation or mutagens such as N-methyl-N-nitro-N-nitrosoguanidine or ethylmethanesulfonate. Accordingly, these artificial mutants and natural mutants involving Streptomyces sp. K93-0711 and strains belonging to the genus Streptomyces and producing K93-0711 I-1 and I-2 can also be used in the present invention.

In the present invention, the K93-0711 I-1 and I-2 producing microorganism belonging to the genus Streptomyces is cultured in conventional media for Streptomyces. Nutrient media containing assimilable carbon sources and nitrogen sources and if required inorganic salts for microorganisms can be used.

Examples of the assimilable carbon sources are glucose, molasses, starch, dextrin, corn steep liquor glycerol and organic acids in combination or alone. Examples of assimilable nitrogen sources are commercially available organic nitrogen such a as peptone, meat extract, yeast extract, dry yeast, soybean powder, corn steep liquor, cotton seed powder, casein, soybean protein hydrolyzates, amino acids and urea, and inorganic nitrogen sources such as nitrates and ammonium salts, in combination or alone.

Further, if necessary, inorganic salts such as sodium, potassium, calcium, magnesium and phosphate can be used. Trace nutrient elements, growth promoters and precursors for K93-0711 I-1 and I-2 production can be added.

Cultivation can proceed with aerobic shake culturing or with aeration culture under aerobic conditions. Industrial production can preferably be carried out by submerged aeration culture. The pH of the medium is preferably neutral. The culture temperature is 20°–37° C., preferably 24°–30° C., and most preferably 27° C. The culturing time is usually 3–6 days in liquid culture, and can be terminated when maximum production for the substance K93-0711 I-1 and I-2 is observed. The culture conditions such as culture medium composition, pH, temperature, stirring and aeration can be adjusted as desired. In liquid culture an anti-foam agent such as a silicone oil, a vegetable oil and surface active agents can be added.

The thus-produced bioactive substance is accumulated in the culture filtrate or the cultured mycelia. The cultured mass is filtered by adding a filter aid such as Celite or Hyflosupercel, or is centrifuged to separate the cultured filtrate and the mycelia. Organic solvent extracts of the cultured filtrate and mycelia were combined and concentrated, and then K93-0711 I-1 and I-2 can be isolated from the extracts.

The cultured mass, without filtration, can be directly extracted with a water-immiscible organic solvent. Extraction of the substance can be carried out from the culture filtrate or from the mycelia if the substance is contained partially in each one.

For purification of K93-0711 I-1 and I-2 from the cultured mass, the organic solvent extracts of the culture filtrate and mycelia are concentrated separately or in combination, then extracted further with a water-immiscible organic solvent such as ethyl acetate or chloroform to transfer K93-0711 I-1 and I-2 to that organic solvent.

The thus-obtained organic solvent extracted layer is, if desired, dehydrated by adding dehydration agents such as anhydrous sodium sulfate and gel beads, and is distilled in vacuo. In this concentrating operation, though the substances K93-0711 I-1 and I-2 are quite stable, the process is preferably performed below 50° C. The substances K93-0711 I-1 and I-2 can be precipitated by adding organic solvent such as hexane or petroleum ether to the residue.

The precipitate is washed several times with hexane, and the crude substances K93-0711 I-1 and I-2 can be separated by vacuum suction or centrifugation. Further purification can be made by various procedures such as employing solvents with a difference in solubilities as to the substances K93-0711 I-1 and I-2 mixed impurities, effecting selective distribution to two liquid phases, and utilizing a difference in absorption on an absorbent carrier. Chromatography is the preferred purification means.

Preferred chromatographic procedures for purification of the substances K93-0711 I-1 and I-2 include absorption chromatography using silica gel, alumina, activated charcoal cellulose, adsorption resin such as hydroxyapatite HP-20; reverse phase distribution chromatography using silanizing silica gel or octadecyl silanizing silica gel; gel filtration chromatography using a molecular sieve such as Sephadex LH-20 or Toyopearl (TM, Toso Corp.) both of which are macroscopic beads of crosslinked polysaccharide dextran; and ion exchange chromatography.

The substances K93-0711 I-1 and I-2 can be purified by using for example chromatography, electrophoresis, countercurrent distribution and ultrafiltration, in combination or alone, in any sequence, or repeatedly. In one embodiment, for example, the crude substance is dissolved in a small amount of chloroform, adsorbed in silica gel, and subjected to chromatography using a chloroform-acetone mixture. The active fraction is concentrated in vacuo, and the concentrate is dissolved in a small amount of methanol. The solution is treated by gel filtration chromatography eluted with methanol to purify the substances K93-0711 I-1 and I-2.

The following example illustrates an especially preferred technique for isolating the compounds of the present invention, but is not to be construed as limiting.

A culture of Streptomyces sp. K93-0711 (FERM BP5764) from an agar slant consisting of 1.0% starch, 0.3% NZ amine, 0.1% yeast extract, 0.1% meat extract, 0.3% calcium carbonate and 1.0% agar, cultured at 27° C. for 6 days, was inoculated into test tubes ($\phi$2×20 cm) containing 10 ml of a medium consisting of 0.1% glucose, 2.4% starch, 0.3% peptone, 0.5% yeast extract, 0.3% meat extract, and 0.4% calcium carbonate (pH 7.0). The test tubes were incubated on a rotary shaker at 200 rpm and 27° C. for 72 hours to prepare a seed culture. The seed culture (2 ml, 2%) was inoculated int a 500 ml Erlenmeyer flask containing 100 ml of the same medium (pH 7.0), and fermented under the same culture conditions. Then 700 ml (1%) of the seed culture was transferred to a 100-liter jar fermenter containing 70 liters of a medium consisting of 2.4% starch, 0.1% glucose, 0.3% peptone, 0.5% yeast extract, 0.3% meat extract, 0.4% calcium carbonate, 0.5% allophosite (100 mesh) and trace metals in solution. The fermentation was carried out at 27° C. for 4 days with agitation and aeration to obtain a cultured mass of approximately 70 liters. Forty liters of ethyl acetate were added to the cultured mass and stirred well, then centrifuged to separate the ethyl acetate layer.

The ethyl acetate extract was concentrated using a rotary evaporator to obtain 11.5 h. crude extract. The crude extract was subjected to silica gel column chromatography (E. Merck, 70-230 mesh), inner diameter 80 mm, column length 260 mm, packed with chloroform. The silica gel column was washed with 1 liter chloroform. The materials were eluted with a mixed solvent of chloroform-methanol (100:1) to obtain an active fraction. The fractions were concentrated in vacuo to yield 561.4 mg of an oily material. The substance was dissolved in small amount of methanol and the solution was subjected to HPLC (Senshu pack PEGACIL, 20×250 mm, solvent 50% acetonitrile-$H_2O$) to obtain 11.8 mg of the substance K93-0711 I-1, and 20.8 mg of K93-7011 I-2.

Analysis of the structure of the substances K93-0711 I-1 and I-2 revealed the compound to be 3a-hydroxyindoline with alkyl-substituted diketocyclopentene at the N position, and more particularly of the following structural formula:

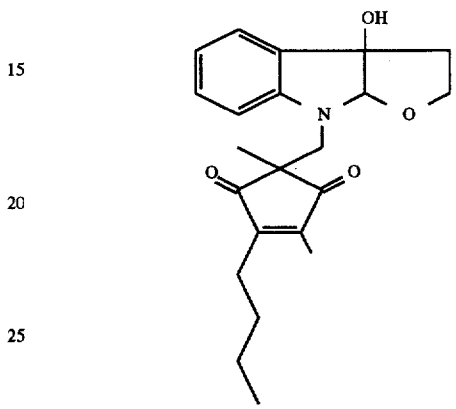

The substances K93-0711 I-1 and I-2 are concluded to be stereoisomers because of the same UV absorption, molecular weight and molecular formula.

Physico-chemical and biological properties of the substances K93-0711 I-1 and I-2 are as follows. Physico-chemical properties:

Bioactive substance K93-7011 I-1

(1) Nature: pale yellow oily substance (2) Molecular formula: $C_{22}H_{27}O_4N$ (high resolution FAB mass spectrum)

(3) Specific rotation $[\alpha]^{24}_D$ +44.4° (c. 0..3, MeOH)

(4) Moleuclar weight: 369 (FAB mass spectrum)

Figure 2:
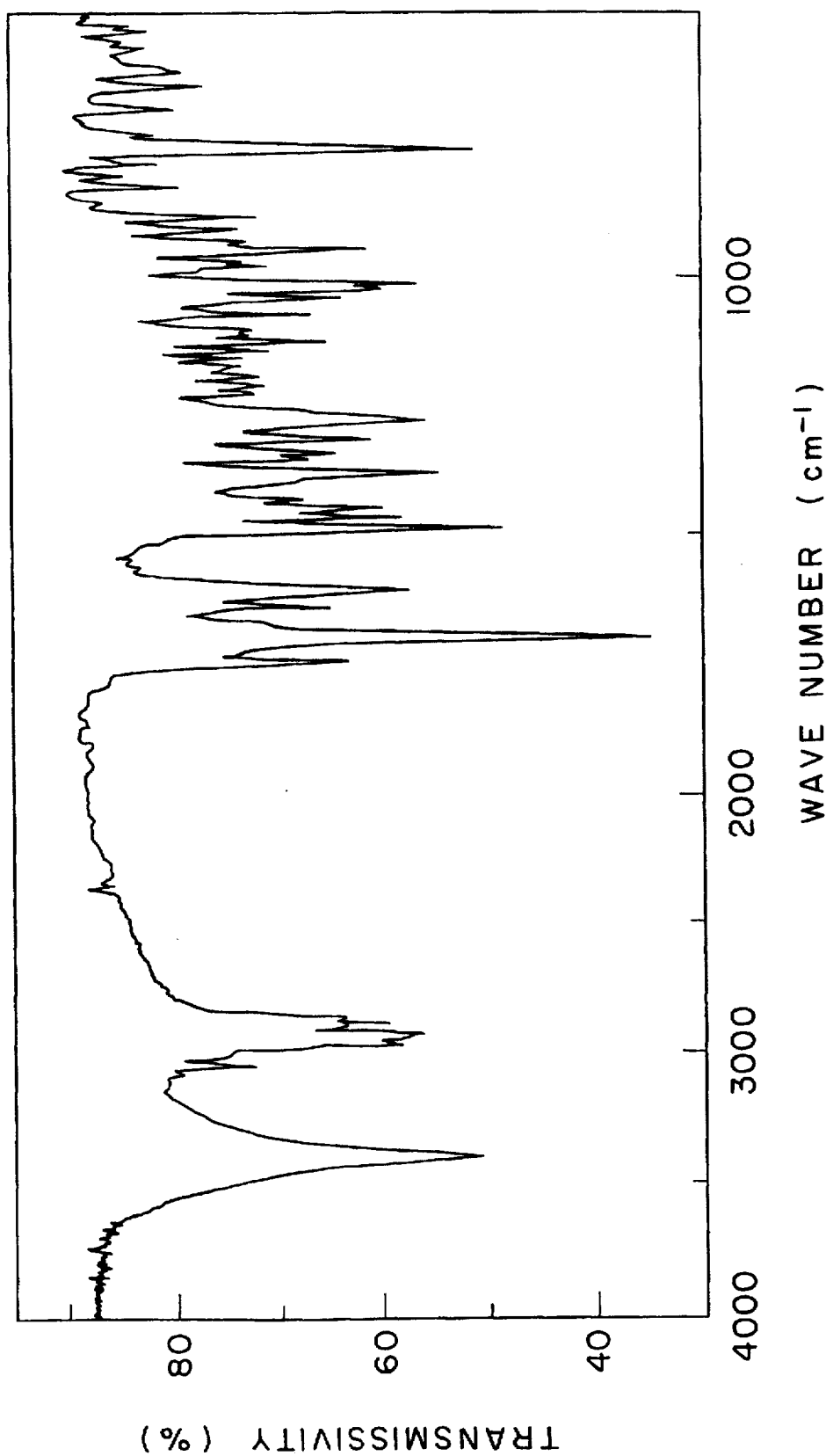
FIG. 2 is the IR absorption spectrum of the bioactive substance K93-0711 I-1 (Br)

(5) Ultraviolet and visible light absorption spectrum: UV spectrum in methanol is shown in FIG. 1 with specific absorption maximum at 299 (log $\epsilon$ 3.28), 245 (log $\epsilon$ 4.26) and 207 (log $\epsilon$ 4.38) nm (6) Infrared absorption spectrum: IR spectrum in KBr is shown in FIG. 2 with absorption bands at 3390, 2927, 1741, 1695, 1603, 1487, 1381, 1281 and 756 $cm^{-1}$ (7) Solubility: Soluble in acetone, ethyl acetate, ethyl ether, hexane, methanol, ethanol, chloroform and benzene Slightly soluble in water (8) Color reaction: positive for sulfuric acid, Ehrlich and iodine.

(9) NMR spectrum: $^1$H-NMR spectrum (in deuterated chloroform, 400 MHz) and $^{13}$C-NMR spectrum (in deuterated chloroform 100.58 MHz)

Figure 3:
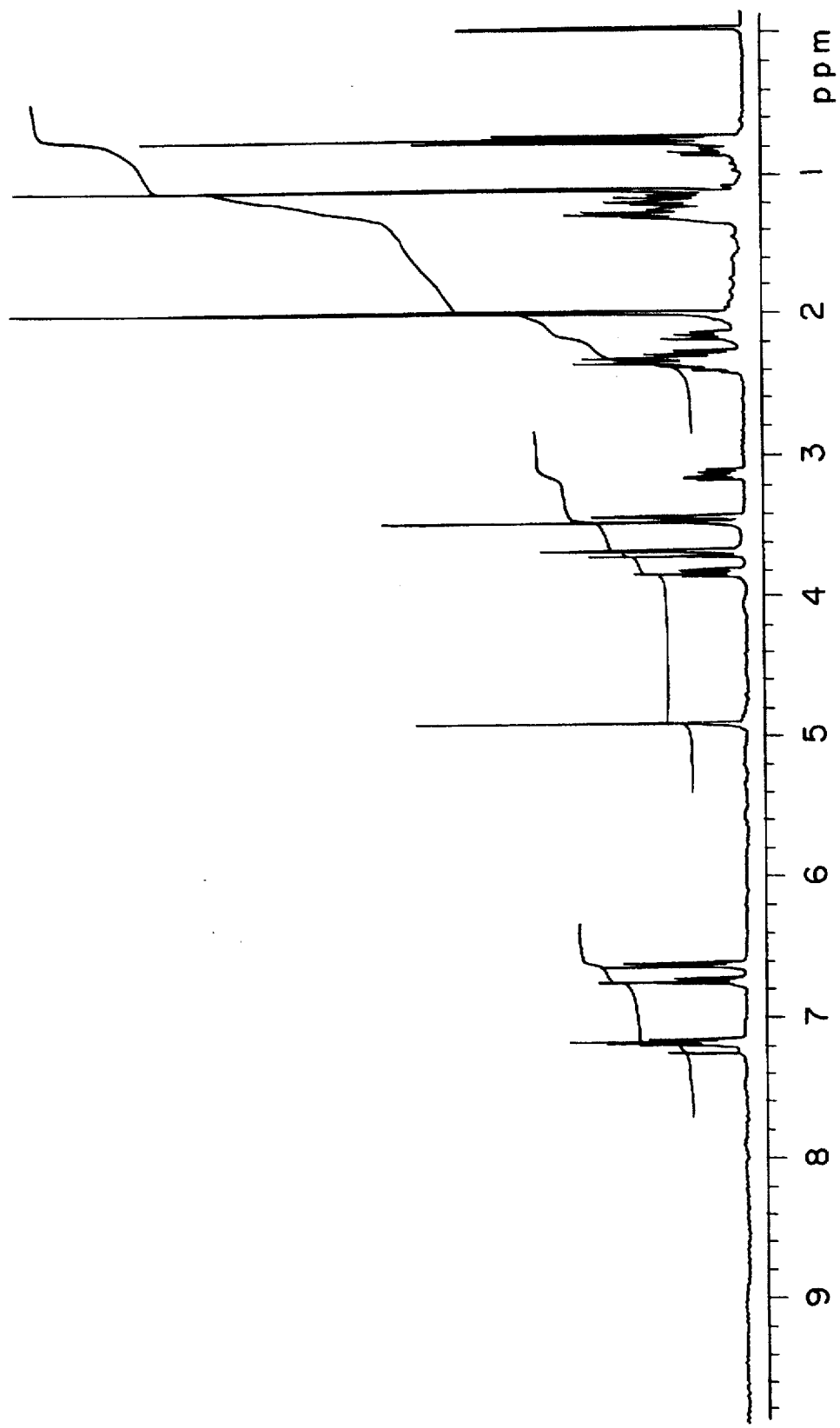
FIG. 3 is the $^1$H-NMR spectrum (in deuterium chloroform, 400 MHz) of K93-0711 I-1.
Figure 4:
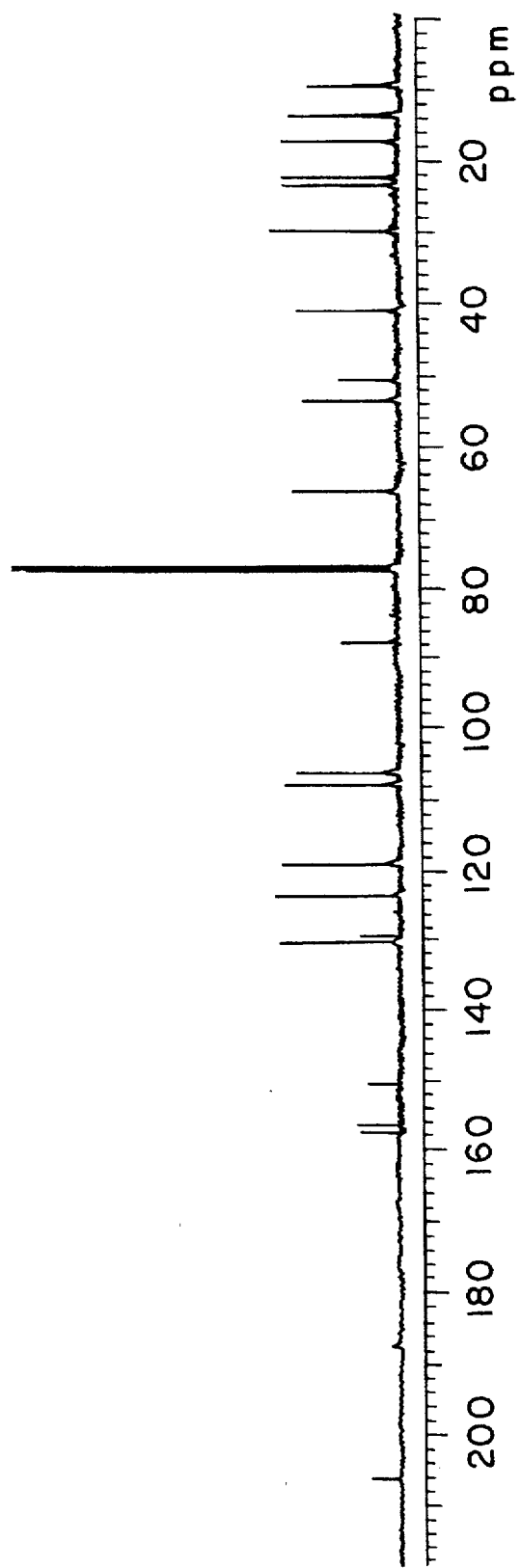
FIG. 4 is the $^{13}$C-NMR spectrum (in deuterium chloroform, 100.58 MHz) of K93-0711 I-1.

(Varian Japan Corp., XL-400 NMR Spectrometer) are shown in FIG. 3 and FIG. 4. Chemical shifts of $^1$H and $^{13}$C are shown in Table 2.

TABLE 2

| $^{13}$C-shift | $^{1}$H-shift(J) |
|---|---|
| 206.4(s) | |
| 206.3(s) | |
| 157.7(s) | |
| 156.6(s) | |
| 150.5(s) | |
| 130.5(d) | 7.19(1H, m) |
| 129.5(s) | |
| 123.5(d) | 7.19(1H, m) |
| 119.1(d) | 6.75(1H, td, 7.3, 0.5) |
| 108.0(d) | 6.63(1H, d, 8.0) |
| 106.2(d) | 4.93(1H, s) |
| 88.0(s) | |
| 66.6(t) | 3.84(1H, m), 3.14(1H, m) |
| 53.7(t) | 3.69(1H, d, 14.2) |
| | 3.45(1H, d, 14.2) |
| 50.6(s) | |
| 41.1(t) | 2.33(1H, dd, 12.0, 9.0) |
| | 2.17(1H, ddd, 12.0, 5.0, 1.5) |
| 29.9(t) | 1.29(2H, m), 1.29 |
| 23.5(t) | 2.38(1H, m), 2.36(1H, m) |
| 22.7(t) | 1.19(2H, m) |
| 17.3(q) | 1.12(3H, s) |
| 13.8(q) | 0.76(3H, t, 7.0) |
| 9.4(q) | 2.00(3H, s) |

Bioactive substance K93-0711 I-2

(1) Nature: pale yellow oily substance (2) Molecular formula: $C^{22}H^{27}O^{4}N$ (high resolution FAB mass spectrum)

(3) Specific rotation $[\alpha]^{24}_D$ +25.6° (c. 0.3, MeOH)

(4) Molecular weight: 369 (FAB mass spectrum)

Figure 5:
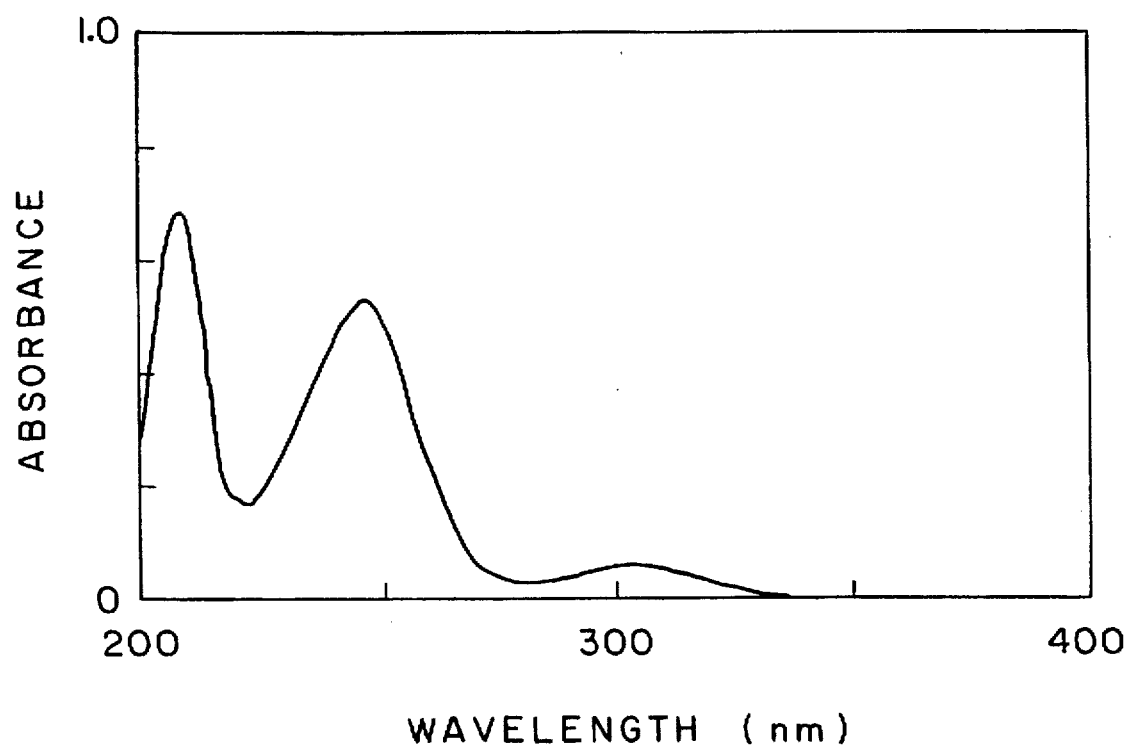
FIG. 5 is the UV absorption spectrum of K93-0711 I-2 (in methanol)
Figure 6:
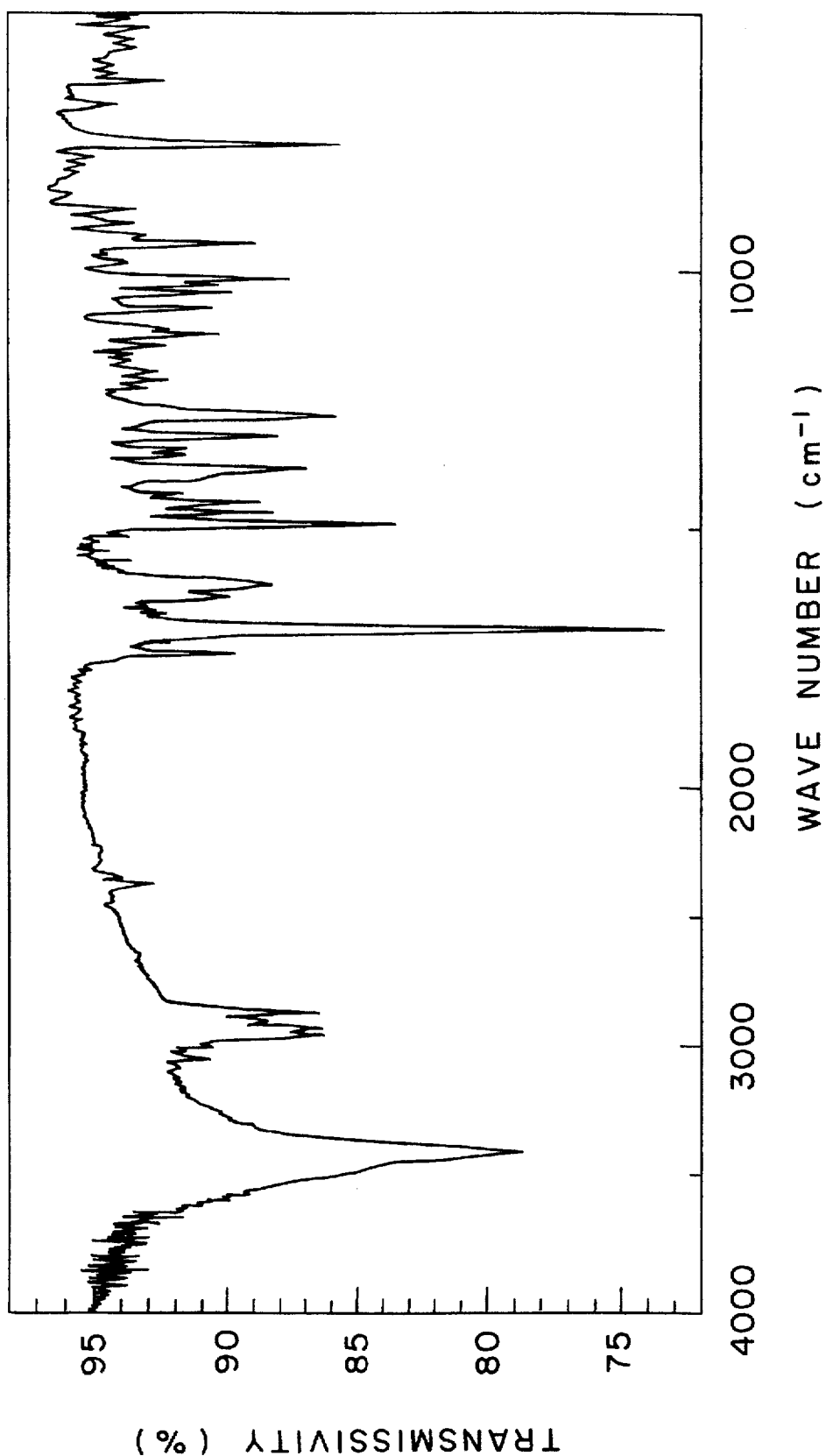
FIG. 6 is the IR absorption spectrum of the bioactive substance K93-0711 I-2 (KBr)

(5) Ultraviolet and visible light absorption spectrum: UV spectrum in methanol is shown in FIG. 5 with specific absorption maximum at 208 (log ε 4.40), 246 (log ε 4.29) and 304 (log ε 3.28) nm (6) Infrared absorption spectrum: IR spectrum in KBr is shown in FIG. 6 with absorption bands at 3410, 2927, 1738, 1693, 1597, 1489, 1380, 1282 and 756 cm$^{-1}$ (7) Solubility: Soluble in acetone, ethyl acetate, ethyl ether, hexane, methanol, ethanol, chloroform and benzene Slightly soluble in water (8) Color reaction: positive for sulfuric acid, Ehrlich and iodine.

(9) NMR spectrum: $^{1}$H-NMR spectrum (in deuterated chloroform, 400 MHz) and $^{13}$C-NMR spectrum (in deuterated chloroform 100.58 MHz)

Figure 7:
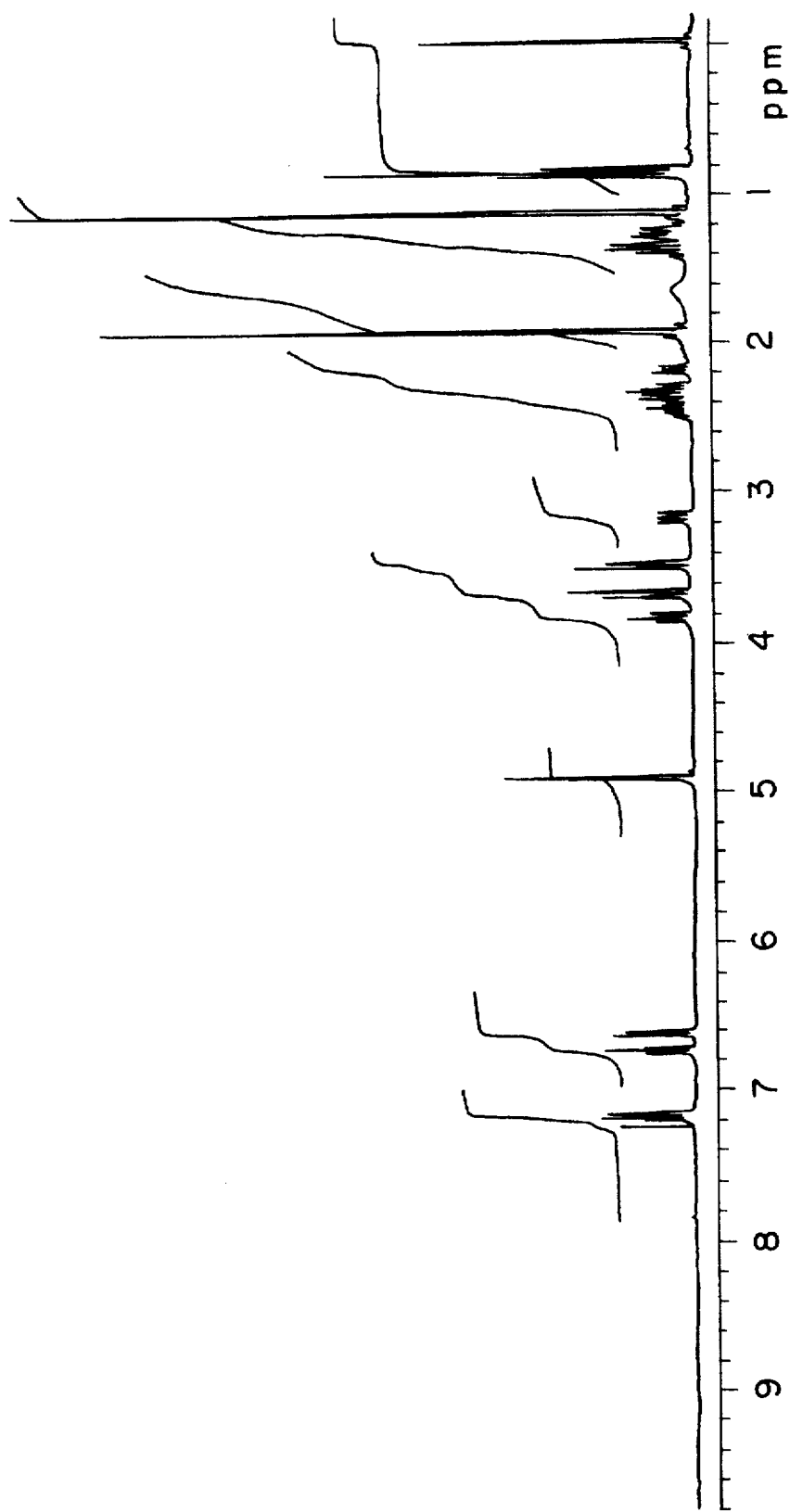
FIG. 7 is the $^1$H-NMR spectrum (in deuterium chloroform, 400 MHz) of K93-0711 I-2.
Figure 8:
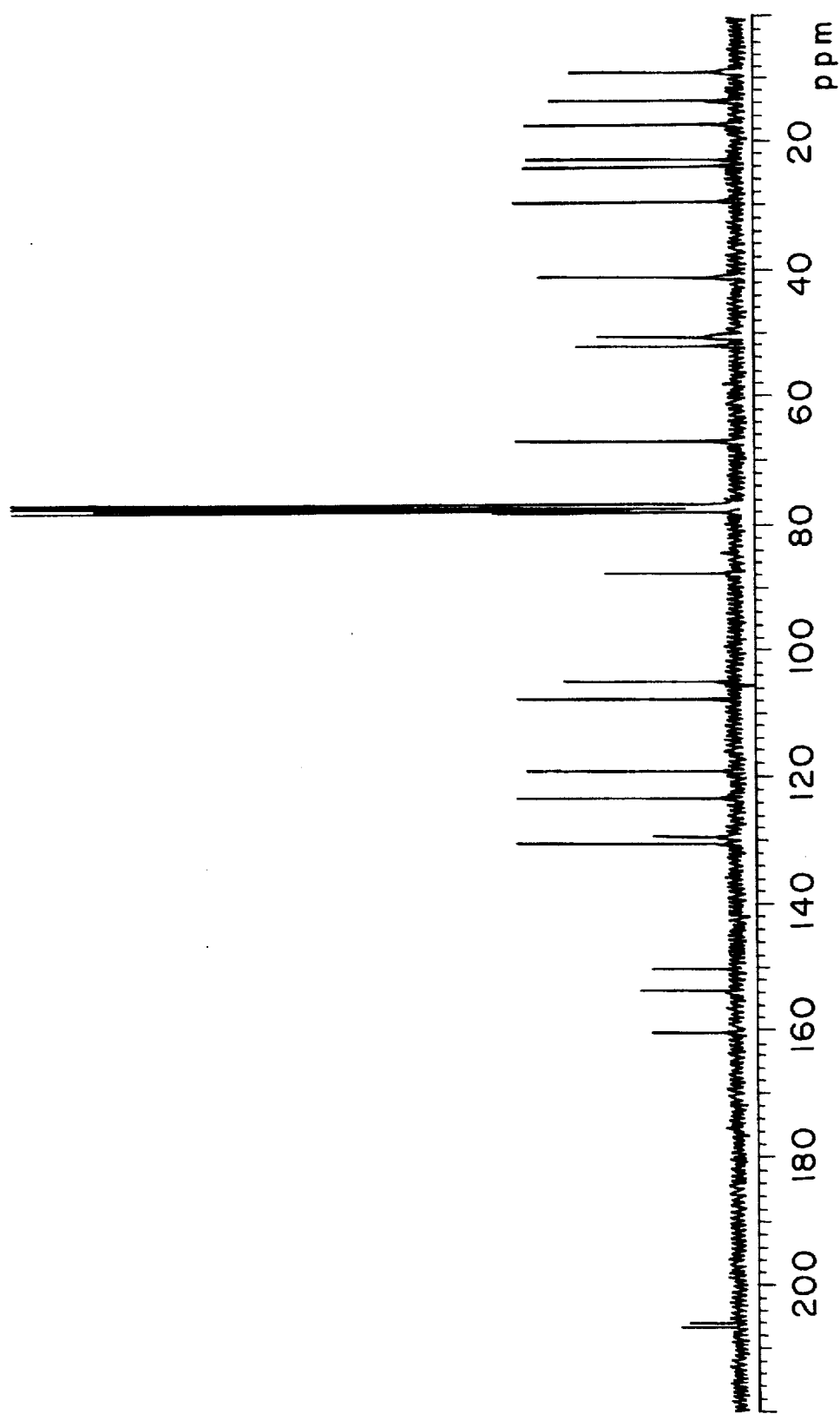
FIG. 8 is the $^{13}$C-NMR spectrum (in deuterium chloroform, 100.58 MHz) of K93-0711 I-2.

(Varian Japan Corp., XL-400 NMR Spectrometer) are shown in FIG. 7 and FIG. 8. Chemical shifts of $^{1}$H and $^{13}$C are shown in Table 3.

TABLE 3

| $^{13}$C-shift | $^{1}$H-shift |
|---|---|
| 206.6(s) | |
| 205.9(s) | |
| 160.3(s) | |
| 153.7(s) | |
| 150.4(s) | |
| 130.5(d) | 7.19(1H, m) |
| 129.4(s) | |
| 123.5(d) | 7.19(1H, m) |
| 118.9(d) | 6.74(1H, td, 7.2, 1.0) |

TABLE 3-continued

| $^{13}$C-shift | $^{1}$H-shift |
|---|---|
| 107.8(d) | 6.62(1H, d, 8.0) |
| 105.0(d) | 4.92(1H, s) |
| 87.9(s) | |
| 66.8(t) | 3.85(1H, ddd, 12.0, 7.9, 1.5) |
| | 3.17(1H, ddd, 12.0, 9.2, 5.0) |
| 52.1(t) | 3.69(1H, d, 14.9) |
| | 3.49(1H, d, 14.9) |
| 50.5(s) | |
| 41.2(t) | 2.33(1H, ddd, 12.0, 7.9, 1.5) |
| | 2.19(1H, ddd, 12.0, 9.2, 1.5) |
| 29.5(t) | 1.39(2H, m) |
| 24.0(t) | 2.46(1H, m), 2.37(1H, m) |
| 22.9(t) | 1.25(2H, m) |
| 17.5(q) | 1.12(3H, s) |
| 13.8(q) | 0.86(3H, t, 7.1) |
| 9.1(q) | 1.94(3H, s) |

Biological properties

Evaluation of IL-6 activity using MH-60 cells MH-60. BSF2 cells (hereinafter designated as MH-60) derived from mouse bone marrow and having IL-6 dependent growth activity were used. IL-6 modification activity as examined using MH-60 by indicating cell growth activity against 0.2 u/ml IL-6. MH-60 cells at a concentration of 5×10³ 100 μl were suspended in RPMI 1640 medium containing 10% fetal bovine serum (FBS) and samples were plated in Δ96 well micro-plate. 5 μl of the bioactive substance K93-0711 I-1 or I-2 was added, and 0.2 u/ml IL-6 solution 100 μl was added to every well, then incubated at 37° C. for 72 hours.

Cells were stained by the MTT method [3-(4, 5-dimethylthiazol-2-yl)-2, 5-diphenyl-2H-tetrazolium bromide], then clorimetrically measured at 492 nm and at 630 nm (reference) to calculate the cell growth rate. Simultaneously, the cell growth rate of IL-6-induced growth of IL-6-independent MH 60 cells established by cloning was measured. The results are shown in Table 4 and Table 5.

TABLE 4

Inhibitory effect of K93-0711 I-1 on growth of MH-60 cells

| Concentration of K93-0711 I-1 (μg/ml) | Growth rate of IL-6 dependent MH-60 cells (%) | Growth rate of IL-6 independent MH-60 cells (%) |
|---|---|---|
| 25.0 | 5.25 | 102.5 |
| 12.5 | 19.85 | 101.2 |
| 6.25 | 35.2 | 97.5 |
| 3.13 | 51.1 | 96.5 |
| 1.56 | 82.1 | 92.3 |
| 0.78 | 88.3 | 100.8 |

TABLE 5

Inhibitory effect of K93-0711 I-2 on growth of MH-60 cells

| Concentration of K93-0711 I-2 (μg/ml) | Growth rate of IL-6 dependent MH-60 cells (%) | Growth rate of IL-6 independent MH-6 cells (%) |
|---|---|---|
| 25.0 | 17.3 | 103.5 |
| 12.5 | 46.3 | 87.8 |

TABLE 5-continued

Inhibitory effect of K93-0711 I-2 on growth of MH-60 cells

| Concentration of K93-0711 I-2 (µg/ml) | Growth rate of IL-6 dependent MH-60 cells (%) | Growth rate of IL-6 independent MH-6 cells (%) |
|---|---|---|
| 6.25 | 70.0 | 99.7 |
| 3.13 | 84.1 | 97.5 |
| 1.56 | 94.3 | 97.8 |
| 0.78 | 91.7 | 102.5 |

As clearly shown in Tables 4 and 5, the bioactive substances K93-0711 I-1 and I-2 of the present invention selectively suppressed IL-6 activity. Therefore, the substance is effective for treatment of diseases involving IL-6, for example treatment of cancer cachexia, multiple myeloma and rheumatoid arthritis.

Although the present invention has been described in connection with various preferred embodiments thereof, it will be appreciated that these embodiments are provided solely for purposes of illustration, and should not be construed as limiting the scope of the invention. Other embodiments and applications of the invention will be readily appaernt to those skilled in the art from reading the present specification and practicing the techniques described herein, without departing whatsoever from the scope and spirit of the appended claims.

References

1. Gideon Strassmann et al., "Mechanism of Experimental Cancer Cachexia, Local Involvement of IL-1 in Colon - 26 Tumor", *J. Immunol.* 150: 2341-2345, 1993.

2. Gideon Strassmann et al., "Evidence for the Involvement of Interleukin 6 in Experimental Cancer Cachexia", *J. Clin. Invest.* 89: 1681-1684, 1992.

3. R. S. Kerbel, "Expression of Multi-cytokine Resistance and Multi Growth Factor Independence in Advanced Stage Metastatic Cancer", Am. J. Pathol. 141, 519-524, 1992.

4. Gideon Strassmann et al., "Mechanism of Experimental Cancer Cachexia, Interaction between Mononuclear Phagocytes and Colon-26 Carcinoma and Its Relevance to IL-6-Mediated Cancer Cachexia", J. Immunol. 148, 3674-3678, 1992.

What is claimed is:

1. A compound of the formula

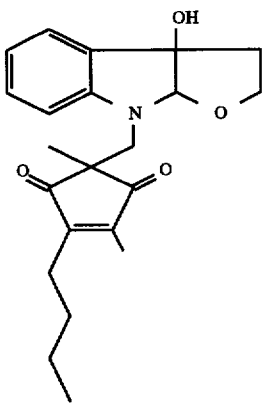

2. The compound of claim 1, which is the stereoisomer K93-0711 I-1, having a specific rotation $[\alpha]^{24}_D +4.44°$ (c. 0.3, MeOH).

3. The compound of claim 1, which is the stereoisomer K93-0711 I-2, having a specific rotation $[\alpha]^{24}_D +25.6°$ (c. 0.3, MeOH).

4. Bioactive substance K930771 I-1 of claim 2, having the following physicochemical properties:

nature: pale yellow oily substance molecular formula: $C_{22}H_{27}O_4N$ as detected by high resolution FAB mass spectrum molecular weight: 369 as detected by FAB mass spectrum ultraviolet and visible ligjt absorption spectra: UV spectrum in methanol as shown in FIG. 1 with specific absorption maxima at 299, log ∈ 3.28; 245, log ∈ 4.26; and 207, log ∈ 4.38 nm infrared absorption spectrum: IR spectrum in KBr as shown in FIG. 2 with absorption bands at 3390, 2927, 1741, 1695, 1603, 1487, 1381, 1281 and 756 $cm^{-1}$ solubility: soluble in acetone, ethyl acetate, ethyl ether, hexane, methanol, ethanol, chloroform and benzene; slightly soluble in water $^1$H—NMR spectrum in deuterated chloroform: as shown in FIG. 3

$^{13}$C—NMR spectrum in deuterated chloroform: as shown in FIG. 4; and color reaction: positive for sulfuric acid, Ehrlich's reagent and iodine.

5. A process for production of bioactive substance K93-0711 I-1and K93-0711 I-2 comprising culturing a microorganism belonging to genus Streptomyces which produces bioactive substances K93-0711 I-1 and K93-0711 I-2 in a medium to accumulate bioactive substance K93-0711 1-1 and K93-0711 I-2 in the medium, and isolating the bioactive substances K93-0711 I-1 and K93-0711 I-2 therefrom.

6. The process according to claim 5 wherein the microorganism is Streptomyces sp. K93-7011.

7. An isolated and biologically purified culture of a microorganism belonging to genus Streptomyces which produces bioactive substances K93-0711 I-1 and K93-0711 I-2.

8. The microorganism according to claim 7 wherein the said microorganism is Streptomyces sp. K93-0711 FERM BP-5764.

9. Bioactive substance K93-0711 I-2 of claim 3, having the following physicochemical properties:

nature: pale yellow oily substance molecular formula: $C_{22}H_{27}O_4N$ as detected by high resolution FAB mass spectrum molecular weight: 369 FAB mass spectrum ultraviolet and visible light absorption spectra: UV spectrum in methanol as shown in FIG. 5 with specific absorption maxima at 304, log ∈ 3.28; 246, log ∈ 4.29; and 208, log ∈ 4.40 nm infrared absorption spectrum: IR spectrum in KBr as shown in FIG. 6 with absorption bands at 3410, 2927, 1738, 1693, 1597, 1489, 1380, 1282 and 756 $cm^{-1}$ solubility: soluble in acetone, ethyl acetate, ethyl ether, hexane, methanol, ethanol, chloroform and benzene; slightly soluble in water $^1$H-NMR spectrum in deuterated chloroform: as shown in FIG. 7

$^{13}$C-NMR spectrum in deuterated chloroform: as shown in FIG. 8; and color reaction: positive for sulfuric acid, Ehrlich's reagent and iodine.

* * * * *